(12) United States Patent
Harrison et al.

(10) Patent No.: US 6,754,537 B1
(45) Date of Patent: Jun. 22, 2004

(54) HYBRID IMPLANTABLE COCHLEAR STIMULATOR HEARING AID SYSTEM

(75) Inventors: William Vanbrooks Harrison, Valencia, CA (US); Janusz A. Kuzma, Parker, CO (US); Alfred E. Mann, Beverly Hills, CA (US); Thomas J. Balkany, Coral Gables, FL (US)

(73) Assignee: Advanced Bionics Corporation, Sylmar, CA (US)

( * ) Notice: Subject to any disclaimer, the term of this patent is extended or adjusted under 35 U.S.C. 154(b) by 0 days.

(21) Appl. No.: 09/979,804

(22) PCT Filed: May 12, 2000

(86) PCT No.: PCT/US00/13122

§ 371 (c)(1), (2), (4) Date: Nov. 13, 2001

(87) PCT Pub. No.: WO00/69512

PCT Pub. Date: Nov. 23, 2000

Related U.S. Application Data (60) Provisional application No. 60/134,289, filed on May 14, 1999.

(51) Int. Cl.[7] ............................................... A61N 1/18
(52) U.S. Cl. ....................................................... 607/57
(58) Field of Search ...................... 600/329; 607/55–57, 607/137

(56) References Cited

U.S. PATENT DOCUMENTS

| | | | |
|---|---|---|---|
| 3,764,748 A | 10/1973 | Branch et al. | 179/107 |
| 5,776,179 A | 7/1998 | Ren et al. | 607/137 |

*Primary Examiner*—Jeffrey R. Jastrzab
(74) *Attorney, Agent, or Firm*—Bryant R. Gold (57) ABSTRACT

A hybrid cochlear implant hearing aid sytem (10) provides low frequency acoustic energy boost, if needed, and high frequency direct neural stimulation. Tinnitus suppression may also be provided. The neurons responsible for sensing high frequency sounds are located at the basal end of the cochlea. A short basal electrode (52) that extends into the cochlea only at the basal region allows direct stimulation of these neurons by an appropriately-controlled cochlear stimulator (50). The basal electrode array typically has from four to eight electrode contacts (54). The design of the electrode array allows the surgeon to place the array using minimally invasive surgical techniques and requires no cochleostomy. The electrode array is thin, and can typically be inserted directly through the round window membrane to make contact with, or to be positioned in close proximity to, the modiolus wall in the basal region of the cochlea. The hybrid implantable cochlear stimulator and hearing aid system relies primarily on the cochlear stimulator portion of the system for being able to sense high frequency sounds, and relies primarily on normal hearing processes, or other acoustic boosting devices and systems, for being able to sense lower frequency sounds.

8 Claims, 4 Drawing Sheets

HYBRID IMPLANTABLE COCHLEAR STIMULATOR HEARING AID SYSTEM

This application claims the benefit of Provisional application Ser. No. 60/134,289 filed May 14, 1999.

BACKGROUND OF THE INVENTION

The present invention relates to hearing aid systems, and more particularly to a hybrid hearing aid system that combines a cochlear stimulator and a hearing aid to provide a hearing aid system that relies primarily on the cochlear stimulator portion of the system for being able to sense high frequency sounds, and that relies primarily on normal hearing processes, or a hearing aid, for being able to sense lower frequency sounds. Such hybrid hearing aid system is best suited for use with a short cochlear electrode array of the type described in applicant's copending patent application, filed concurrently herewith, entitled "Electrode Array for Hybrid Cochlear Stimulator" (Attorney Docket Number AB-084-PC), which application is incorporated herein by reference.

A hybrid cochlear stimulation system provides electrical stimulation only to the basal end of the cochlea to stimulate ganglion cells responsible for sensing higher-frequency sounds, and relies on normal hearing (activation of hair cells through fluid motion within the cochlea), which may occur with or without the assistance of a conventional or a custom hearing aid, to sense middle-to-lower frequency sounds.

Hearing loss is generally of two types: conductive and sensorineural. Of these, conductive hearing loss occurs where the normal mechanical pathways for sound to reach the hair cells in the cochlea are impeded, for example, by damage to the ossicles. Conductive hearing loss may often be helped by use of conventional hearing aids, which amplify sound so that acoustic information does reach the cochlea and the hair cells. Some types of conductive hearing loss are also amenable to alleviation by surgical procedures.

Sensorineural hearing loss, on the other hand, results due to the absence or the destruction of the hair cells in the cochlea which are needed to transduce acoustic signals into auditory nerve impulses. Persons who suffer from sensorineural hearing loss are unable to derive any benefit from conventional hearing aid systems, no matter how loud the acoustic stimulus is made, because their mechanisms for transducing sound energy into auditory nerve impulses have been damaged. Thus, in the absence of properly functioning hair cells, there is no way auditory nerve impulses can be generated directly from sounds.

To overcome sensorineural deafliess, there have been developed numerous cochlear implant systems—or cochlear prosthesis—which seek to bypass the hair cells in the cochlea by presenting electrical stimuli directly to the ganglia of the auditory nerve located adjacent the modiolar wall of the cochlea. When triggered, the ganglia, also referred to as ganglion cells send nerve impulses to the brain via the auditory nerve, leading to the perception of sound in the brain, and an at least partial restoration of hearing function. The common denominator in these cochlear prosthesis systems has been the implantation into the cochlea of electrodes which are responsive to a suitable external source of electrical stimuli and which are intended to transmit those stimuli to the ganglion cells, and thereby to the auditory nerve fibers.

As people age, they frequently experience progressive hearing loss. Usually this loss is more prevalent and more sever at higher frequencies. Thus, it is estimated that a large segment of the hearing-impaired population exhibit sensorineural hearing loss relative to high frequency sounds, but maintain the ability to transduce middle-to-lower frequency sounds through functioning hair cells.

The usual method to restore this high frequency hearing loss is by using a hearing aid that increases the amplitude of the acoustic energy applied to the tympani membrane. Although effective, this approach does not provide the same level of restoration to high frequencies as it does to lower frequencies. Also, the increase in acoustic amplitudes used in this method can ofttimes further degrade residual hearing, resulting in a further decrease in the ability to hear the higher frequencies.

It is thus evident that there is thus a need for a "hybrid" cochlear stimulation system that electrically stimulates only the ganglion cells responsible for sensing higher frequency sounds, while allowing or permitting the normal hearing process (e.g., activation of hair cells through wave motion of the fluid within the cochlea) to function for the purpose of sensing lower-to-middle frequency sounds.

A cochlear prosthesis operates by direct electrical stimulation of the auditory nerve cells, bypassing the defective cochlear hair cells that normally transduce acoustic energy into electrical activity in such nerve cells. Because the ganglion cells responsible for sensing higher frequency sounds are all generally located in or near the basal end of the cochlea (the end of the cochlea nearest the basal membrane), a hybrid cochlear stimulation system thus requires an electrode array that can be inserted within the cochlea a sufficient depth to be near such cells, but which also does not block or significantly interfere with the normal functioning of the cochlea for hair cells located deeper within the cochlea. Thus, there is a need for such an electrode array that may be used with a hybrid implantable cochlear stimulator hearing aid system.

SUMMARY OF THE INVENTION

The present invention addresses the above and other needs by providing a hybrid implantable cochlear stimulator and hearing aid system that relies primarily on the cochlear stimulator portion of the system for being able to sense high frequency sounds, and that relies primarily on normal hearing processes, or other acoustic boosting devices and systems, for being able to sense lower frequency sounds. Such hybrid hearing aid system uses a relatively short and unobtrusive cochlear electrode array, e.g., of 6–8 nun in length, of the type described in applicant's copending patent application, previously referenced, entitled "Electrode Array for Hybrid Cochlear Stimulator" (Attorney Docket Number AB-084-PC), or something equivalent thereto.

A hybrid cochlear implant hearing aid system in accordance with the present invention provides low frequency acoustic energy boost, if needed, and high frequency direct neural stimulation. The high frequency neurons are located at the basal end of the cochlea, providing easy access for the surgical placement of a short electrode that stimulates only the high frequencies. The electrode array typically has from four to eight electrode contacts, e.g., 4 or 5 electrode contacts. The design of the electrode array allows the surgeon to place the array using minimally invasive surgical techniques and requires no cochleostomy. The electrode array is thin, and can typically be inserted directly through the round window membrane to make contact with, or to be positioned in close proximity to, the modiolus wall in the basal region of the cochlea.

The front-end amplifier and processor and spectral decomposition filters used with the hybrid system of the present invention may be the same for both acoustic boost and neural stimulation applications. The frequencies are separated and sent to circuits that either convert them into mechanical vibrations to boost low-to-middle frequency acoustic energy, or into high frequency energy that is further divided and converted to stimulation pulses that are applied directly to the neurons located in the basal region of the cochlea through the short electrode. A smoothing circuit may be provided to allow a smooth, seamless transition from the acoustic enhancement provided for low-to-middle frequencies and the neural stimulation provided for the high frequencies.

In accordance with one aspect of the invention, tinnitus (which is a buzzing, or ringing, sound in the ear) is suppressed by delivering special pulse sequences on some of the electrodes located in the basal region of the cochlea, while acoustic enhancement is provided in the low frequency range.

Advantageously, the hybrid system of the present invention may be used for several applications. Such applications include, but are not limited to:

(a) high frequency neural stimulation combined with residual low frequency hearing;

(b) high frequency neural stimulation signal enhancement combined with low frequency acoustic signal enhancement;

(c) tinnitus suppression;

(d) tinnitus suppression combined with acoustic signal enhancement;

(e) high frequency neural stimulation signal enhancement, acoustic signal enhancement, and tinnitus suppression stimulation; or (f) tinnitus suppression combined with cochlear neural stimulation.

It is thus a feature of the present invention to provide a hybrid cochlear stimulation and hearing aid system that restores hearing function over a wide frequency band, e.g., from low frequencies to high frequencies.

It is a further feature of the invention to provide such a hybrid system wherein minimally invasive surgical techniques are employed.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components or elements throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
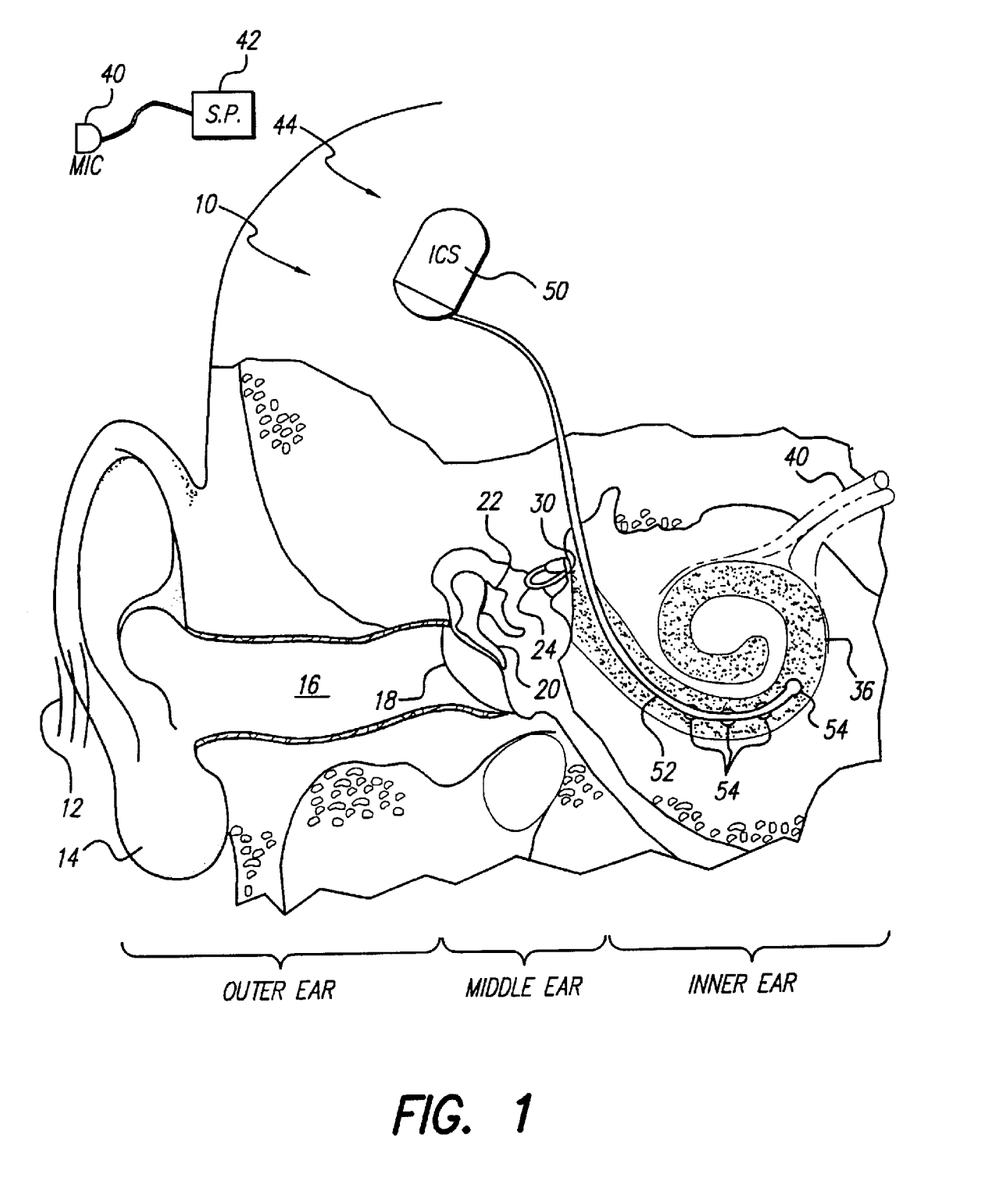
FIG. 1 is a functional schematic diagram of the ear, showing the manner in which an implantable cochlear stimulator and short cochlear electrode in the basal region of the cochlea may be used to practice the invention in accordance with one embodiment thereof.

Turning first to FIG. 1, one embodiment of the hybrid cochlear stimulation system of the present invention is shown. Such embodiment relies upon an implantable cochlear stimulator (ICS) 50 to provide direct electrical stimulation of the ganglion cells located at the basal end of the cochlea, to thereby enhance the hearing of high frequency sounds; and relies upon the patient's normal hearing processes, e.g., the patient's residual low and mid frequency hearing, to sense low-to-mid frequency sounds.

As seen in FIG. 1, the major relevant components of the outer, middle and inner ear are illustrated. To better understand the present invention, It will first be helpful to briefly review the normal operation of a fully functional ear. Thus, as seen in FIG. 1, the outer ear includes the auricle 14 and the ear canal 16. An acoustic pressure wave, or sound wave, represented in FIG. 1 by the short parallel lines 12, is collected by the auricle 14 and funneled into the ear canal 16. At the end of the ear cannel 16 is the "ear drum" 18, or in medical terms, the tympanic membrane 18. In a person who is not significantly hearing impaired, the received acoustic wave 12 causes the tympanic membrane 18 to vibrate, which vibration is coupled through three tiny bones, the malleus ("hammer") 20, the incus ("anvil") 22 and the stapes ("stirrup") 24, to the fenestra 30.

In anatomical terms, the fenestra comprises an opening resembling a window. The *fenestra ovalis*, or oval window, is the opening between the middle ear and the vestibule of the inner ear. It is closed by a membrane to which the stapes is attached. The *fenestra rotunda*, or round window, is the opening between the scala tympani of the cochlea and the middle ear. The round window is also closed by a membrane, which for purposes of the present application, may be referred to as the round window membrane. For purposes of the schematic diagram shown in FIG. 1, as well as the other figures presented herein, the function of both the oval window and round window is represented by the single membrane 30.

The bones of the middle ear serve to filter and amplify the perceived acoustic wave 12, causing the fenestra membrane 30 to articulate, or vibrate, in response to the acoustic wave 12. Vibration of the membrane 30 sets up waves of fluid motion within the fluid contained within the snail-shaped cochlea 36. Such fluid motion, in turn, activates tiny hair cells (not shown in FIG. 1) that line the inside of the cochlea 36. Activation of the hair cells causes appropriate nerve impulses to be transferred through the spiral ganglion 40 to the brain, where they are perceived as sound.

The spiral ganglion cells that are responsible for the perception of high frequency sounds are generally located at the basal end of the cochlea 36, i.e., that end of the cochlea closest to the membrane 30. For those individuals who suffer from high frequency hearing loss, the hair cells in the basal region of the cochlea are ineffective or otherwise damaged to the point where it is not possible to activate them. Hence, in accordance with the present invention, an implantable cochlear stimulator (ICS) 50 may be implanted near the ear, and a short cochlear electrode array 52, having a plurality of spaced apart electrodes 54 thereon, is inserted into the cochlea 36 through the membrane 30. (In practice, the electrode array 52 may be inserted directly through a slit made in the round window.) Such ICS 50 is coupled to a microphone, e.g., an external microphone 40 (although an internal, i.e., implanted, microphone could also be used) that senses sounds. The microphone signals are amplified and processed by a suitable speech processor (S. P.) 42, which S. P. may also be external or implanted. The speech processor generates appropriate control signals that are coupled to the ICS 50. Such coupling may occur through various means, but is usually achieved through an inductive coupling link, represented by the arrow 44, with an external head piece, connected to the speech processor 42. Such link also provides a way for power to be coupled into the implanted ICS 50. However, it is also possible for the processor and power source to be implanted, either as an integral part of the ICS 50 or in a separate housing coupled to the ICS. (See, e.g., International Publication No. WO 99/06108, published Feb. 11, 1999, incorporated herein by reference.)

In operation, the speech processor 42 functions as a signal processing means for processing the electrical signals received from the microphone and for generating high-frequency control signals therefrom representative of the higher frequency content of the sensed acoustic sounds. These control signals are then coupled to the ICS 50 through the link 44. The ICS 50 has means responsive to the high-frequency control signals for selectively generating electrical stimuli and applying the electrical stimuli to the electrode (52). In this manner, the basal region of the scala tympani duct is stimulated with electrical stimuli representative of the higher-frequency content of the sensed acoustic sounds.

In accordance with the embodiment of the invention depicted in FIG. 1, the sounds sensed by the microphone 40 are processed and filtered to separate out the high frequency sounds. These high frequency sounds are then converted to appropriate electrical stimuli that are selectively applied to the electrode contacts 54 of the electrode array 52 positioned in the basal region of the cochlea. Such electrical stimuli bypass the defective hair cells in the basal region of the cochlea and directly activate the nerves within the of the spiral ganglion, causing nerve impulses to be transferred to the brain, where they may be perceived as high frequency sounds.

The other hair cells in the cochlea, i.e., those in the apical and mid regions of the scala tympani duct, retain their functionality. That is, these hair cells are able to sense the fluid waves set up by vibrations of the membrane 30 corresponding to low-to-mid frequency sounds. Hence, the patient (or user of the hybrid system shown in FIG. 1) is able to sense high frequency sounds through the ICS portion of the system, and is able to sense lower frequency sounds through the normal hearing processes of the ear.

Figure 2:
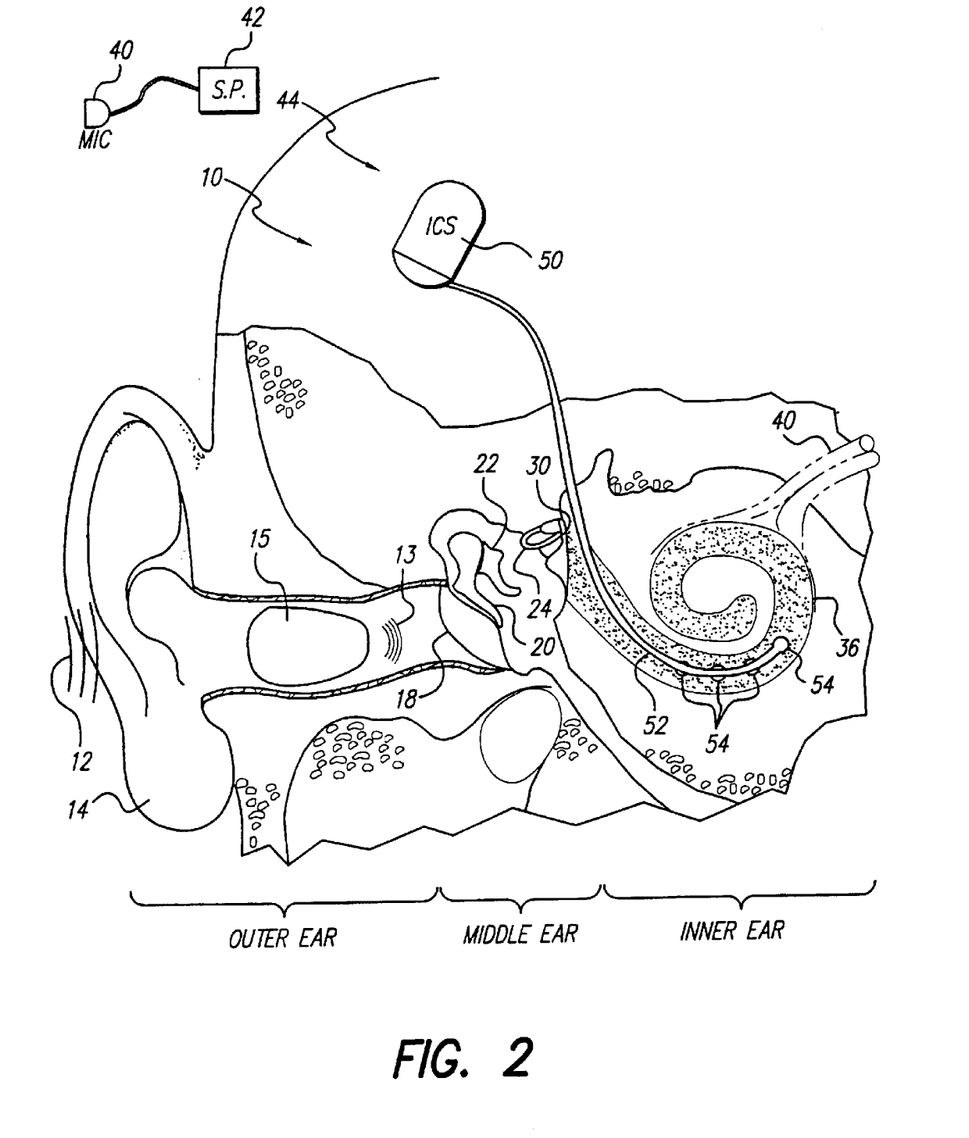
FIG. 2 is a functional schematic diagram of the ear as in FIG. 1, and further shows the manner in which a conventional in-the-ear hearing aid may be used to supplement the practice of the invention.

In FIG. 2, another embodiment of the invention is depicted. The embodiment shown in FIG. 2 is the same as the embodiment shown in FIG. 1 except for the addition of an in-the-canal hearing aid 15. The in-the-canal hearing aid 15, which may be of conventional design, receives the acoustic waves 12 and amplifies them, thereby presenting amplified acoustic waves 13 to the tympanic membrane 18. The amplified acoustic waves 13 are thereby able to increase the magnitude of the vibrations that pass through the middle ear and articulate the membrane 30, thereby increasing the magnitude of the fluid waves within the cochlea, which higher-magnitude fluid waves may be more effective at activating the hair cells throughout the cochlea. Typically, however, the high-frequency hair cells at the basal end of the cochlea remain defective and unresponsive to the higher-magnitude fluid waves. Thus, the cochlear stimulator portion (ICS 50 and electrode array 52) of the hybrid system must still be used if high frequency sounds are to be perceived.

Figure 3:
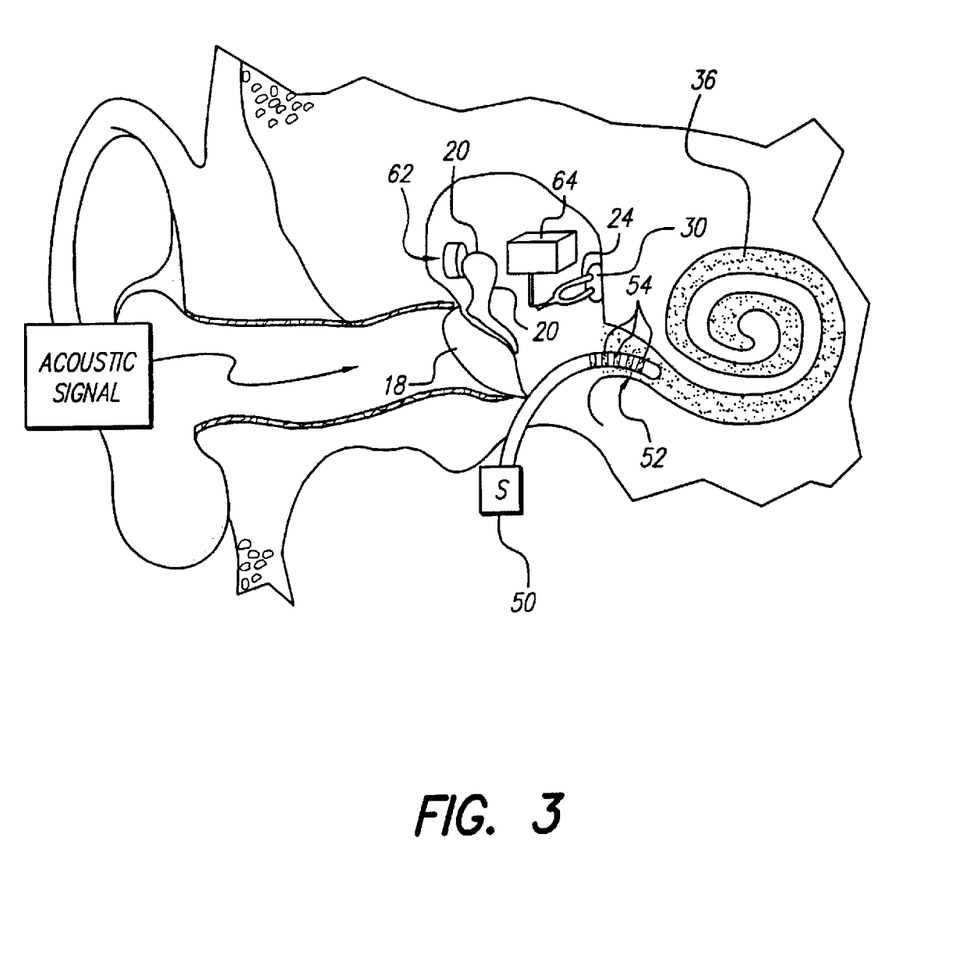
FIG. 3 is a functional schematic diagram of the ear as in FIGS. 1 and 2, and further shows how a middle-ear acoustic boosting system or hearing-aid device may be used as part of the hybrid system of the invention.

Turning next to FIG. 3, yet another embodiment of the invention is shown, comprising a middle ear hearing aid system 60 which is inserted into the middle ear. Such system 60 includes an implanted acoustic microphone 62 attached to the malleus 20 and an implanted acoustic amplifier and driver 64 coupled to the stapes 24. Thus, as acoustic signals vibrate the tympanic membrane, such signals are sensed by the microphone 62 attached to the malleus 20 and transduced to an electrical or other (e.g., optical or magnetic) signal. This signal is then applied to the acoustic amplifier and driver device 64, where they are transduced back to mechanical vibrations that drive the stapes 24, and hence vibrate the membrane 30 with an amplified or increased intensity. The vibration of the membrane 30 with an increased intensity or magnitude, in turn, increases the intensity of the fluid waves that are set up within the scala tympanic duct of the cochlea, thereby more effectively activating the non-defective hair cells throughout the cochlea. For a hearing impaired individual, having defective high frequency hair cells, such middle ear hearing aid system 60 thus provides an increased ability to sense lower frequency acoustic signals. To sense high frequency sounds, a stimulator circuit 50', coupled to the basal electrode array 52, senses the high frequency sounds and converts them to appropriate electrical stimuli for application to the respective electrode contacts 54 on the electrode array 52.

Figure 4:
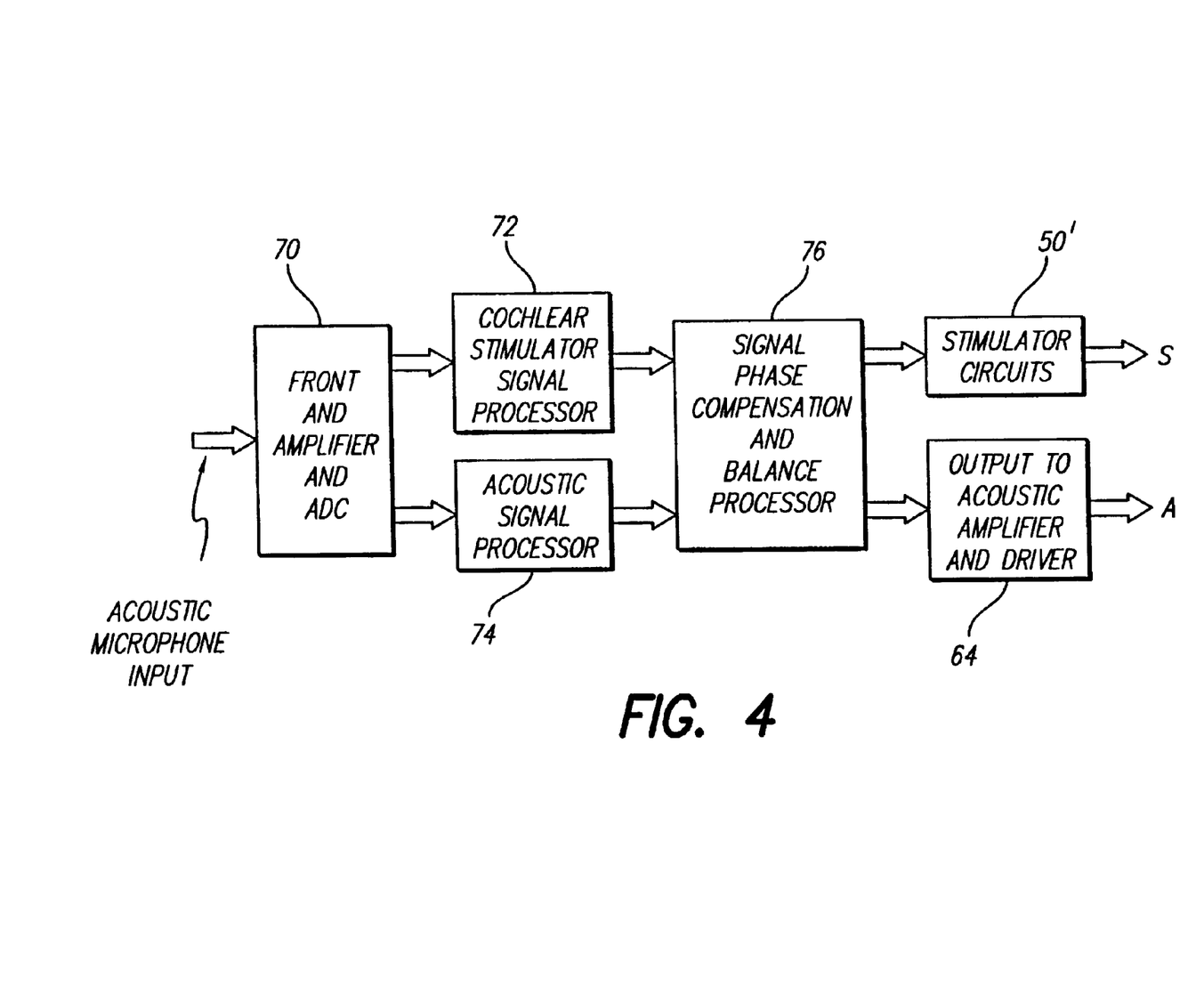
FIG. 4 is a block diagram of the signal processing portions of the invention.

Turning next to FIG. 4, a block diagram of the signal processing circuits used by the hybrid system of FIG. 3 is depicted. As seen in FIG. 4, a front-end amplifier and processor 70, including an analog-to-digital converter (ADC), senses acoustic signals. The processor further uses appropriate spectral decomposition filters to separate the high frequency signal components from the low and middle frequency components. The high frequency signal components are then sent to a cochlear signal processor 72, and the low and middle frequency signal components are sent to an acoustic signal processor 74. Each of these processors 72 and 74 applies appropriate signal processing strategies to the signals and then applies them to a signal phase compensation and balance processor 76. This phase compensator and balance processor performs, inter alia, a smoothing function that allows a smooth, seamless transition from the acoustic enhancement provided for low-to-middle frequencies and the neural stimulation provided for the higher frequencies. After balancing and phase compensation, which may be considered as "signal enhancement", the acoustic signals are sent to the output-to-acoustic amplifier and driver circuit 64 and the cochlear stimulator signals are sent to the stimulator circuits 50'. At the output-to-acoustic amplifier and driver circuit 64, the signals are converted into mechanical vibrations to boost low-to-middle frequency acoustic energy. At the cochlear stimulator circuits 50', the signals are converted into high frequency energy that is further divided and converted into stimulation pulses that are applied directly to the neurons located in the basal region of the cochlea through the short basal electrode 52.

One important aspect of the invention relates to its ability to suppress tinnitus. Tinnitus suppression is carried out by generating appropriate pulse sequences in the stimulator 50 or 50' and then delivering these pulse sequences to selected electrodes 54 on the electrode array 52. Such suppression may occur at the same time that acoustic enhancement takes place for the lower frequencies.

The various components of the invention, i.e., high frequency neural stimulation, residual lower frequency hearing, high frequency neural stimulation with signal enhancement, lower frequency acoustic signal enhancement, and tinnitus suppression, may advantageously be combined in various ways to address several different applications. For example, the invention may be used for any or all of the following applications:

(a) high frequency neural stimulation combined with residual lower frequency hearing;

(b) high frequency neural stimulation signal enhancement combined with lower frequency acoustic signal enhancement;

(c) tinnitus suppression;

(d) tinnitus suppression combined with acoustic signal enhancement;

(e) higher frequency neural stimulation signal enhancement, acoustic signal enhancement, and tinnitus suppression stimulation; or (f) tinnitus suppression combined with cochlear neural stimulation.

As described above, it is thus seen that the present invention provides a versatile hybrid cochlear stimulation and hearing aid system that may restore hearing function over a wide frequency band, e.g., from low frequencies to high frequencies.

As described above, it is further seen that the invention provides such a hybrid system wherein minimally invasive surgical techniques need be employed.

As described above, it is additionally seen that the invention provides a versatile hybrid system that can be used for a wide variety of applications, ranging from higher frequency neural stimulation, with or without signal enhancement (balancing, smoothing and phase compensation); tinnitus suppression; residual lower frequency hearing, or lower frequency acoustic signal enhancement.

While the invention herein disclosed has been described by means of specific embodiments and applications thereof, numerous modifications and variations could be made thereto by those skilled in the art without departing from the scope of the invention set forth in the claims.

What is claimed is:

1. A hybrid cochlear stimulator and hearing aid system comprising:

a short cochlear electrode array, having a plurality of spaced apart electrodes thereon; adapted for insertion into the basal region of the scala tympani duct of a human cochlea;

an implantable stimulator electrically connected to the electrodes on the short cochlear electrode array;

microphone means for sensing acoustic sounds and converting the sensed acoustic sounds to electrical signals; and signal processing means for processing the electrical signals and generating high-frequency control signals therefrom representative of the higher frequency content of the sensed acoustic sounds;

the implantable stimulator having means responsive to the high-frequency control signals generated by the signal processing means for selectively generating electrical stimuli and applying the electrical stimuli to the electrodes of the electrode array, whereby the basal region of the scala tympani duct is stimulated with electrical stimuli representative of the higher-frequency content of the sensed acoustic sounds.

2. The hybrid system of claim 1 further including an acoustic boost device for amplifying the lower frequency content of the sensed acoustic sounds.

3. The hybrid system of claim 2 further including compensation and balancing means for providing a smooth transition from lower frequencies sensed with the aid of the acoustic boost device to the higher frequencies stimulated through the short cochlear electrode array and implantable stimulator.

4. The hybrid system of claim 2 wherein the acoustic boost device comprises a hearing aid adapted to be placed in the ear canal of a user.

5. The hybrid system of claim 2 wherein the acoustic boost device comprises a middle ear hearing aid system.

6. The hybrid system of claim 5 wherein the middle ear includes a malleus and a stapes, and wherein the middle ear hearing aid system includes an implantable acoustic microphone adapted to be coupled to the malleus, and an implanted acoustic amplifier and driver adapted to be coupled to the stapes.

7. The hybrid system of claim 6 wherein the middle ear hearing aid system and the signal processing means share common front-end processing circuitry.

8. The hybrid system of claim 1 further including means coupled with the signal processing means for generating specific sequences of electrical stimulation pulses applied through the electrodes on the short cochlear electrode array that suppress tinnitus.

* * * * *

UNITED STATES PATENT AND TRADEMARK OFFICE
Certificate

Patent No. 6,754,537 B1            Patented: June 22, 2004

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: William Vanbrooks Harrison, Valencia, CA (US); Janusz A. Kuzma, Parker, CO (US); Alfred E. Mann, Beverly Hills, CA (US); Thomas J. Balkany, Coral Gables, FL (US); and Bruce J. Gantz, Iowa City, IA (US)

Signed and Sealed this Thirty-first Day of January 2012.

JINHEE LEE
*Supervisory Patent Examiner*
Art Unit 2835
Technology Center 2800

UNITED STATES PATENT AND TRADEMARK OFFICE
Certificate

Patent No. 6,754,537 B1                                      Patented: June 22, 2004

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: William Vanbrooks Harrison, Valencia, CA (US); Janusz A. Kuzma, Parker, CO (US); Alfred E. Mann, Beverly Hills, CA (US); Thomas J. Balkany, Coral Gables, FL (US); and Bruce J. Gantz, Iowa City, IA (US).

Signed and Sealed this Thirteenth Day of March 2012.

<div style="text-align:right">

NIKETA I. PATEL
*Supervisory Patent Examiner*
Art Unit 3762
Technology Center 3700

</div>